(12) United States Patent
Leight

(10) Patent No.: US 12,370,089 B2
(45) Date of Patent: *Jul. 29, 2025

(54) COMPRESSIBLE FIT EARPLUG WITH PLANAR INSERT

(71) Applicant: Hearos, LLC, Latham, NY (US)

(72) Inventor: Howard S. Leight, Santa Monica, CA (US)

(73) Assignee: HEAROS, LLC, Latham, NY (US)

( * ) Notice: Subject to any disclaimer, the term of this patent is extended or adjusted under 35 U.S.C. 154(b) by 189 days.

This patent is subject to a terminal disclaimer.

(21) Appl. No.: 17/406,927

(22) Filed: Aug. 19, 2021

(65) Prior Publication Data

US 2021/0386591 A1 Dec. 16, 2021

Related U.S. Application Data

(62) Division of application No. 16/107,434, filed on Aug. 21, 2018.

(51) Int. Cl.
*A61F 11/08* (2006.01)

(52) U.S. Cl.
CPC .................................. *A61F 11/08* (2013.01)

(58) Field of Classification Search
CPC .............. A61F 11/085; A61F 2011/085; A61F 2011/145; A61F 11/14; A61F 11/06–12; G10K 11/16; G10K 11/162; G10K 11/168; G10K 11/178; H04R 2225/023; H04R 2225/025; H04R 1/10; H04R 1/1016; H04R 25/652
USPC .................................... 128/864; 181/134–135
See application file for complete search history.

(56) References Cited

U.S. PATENT DOCUMENTS

| | | | |
|---|---|---|---|
| 2,888,921 A | 6/1959 | Nielson et al. | |
| 3,811,437 A | 5/1974 | Gardner | |
| RE29,487 E | 12/1977 | Gardner | |
| 5,074,375 A * | 12/1991 | Grozil | A61F 11/12 |
| | | | 181/135 |
| 5,195,539 A | 3/1993 | Dyrud et al. | |
| 5,799,658 A | 9/1998 | Falco | |
| 6,006,857 A | 12/1999 | Leight et al. | |
| 7,192,544 B2 | 3/2007 | Jenkins, Jr. et al. | |
| 7,464,786 B2 | 12/2008 | Falco et al. | |
| 8,770,338 B1 | 7/2014 | Duncan et al. | |
| 8,870,558 B2 | 10/2014 | Schumaier et al. | |
| 10,441,471 B2 | 10/2019 | Endle et al. | |
| 10,610,413 B2 | 4/2020 | Gilder et al. | |

(Continued)

FOREIGN PATENT DOCUMENTS

| | | |
|---|---|---|
| WO | 0054712 A1 | 9/2000 |
| WO | 2004021941 A1 | 3/2004 |

OTHER PUBLICATIONS

Property Information—Young's Modulus (Year: 2023).*

(Continued)

*Primary Examiner* — Caitlin A Carreiro
(74) *Attorney, Agent, or Firm* — Fredrikson & Byron, P.A.

(57) ABSTRACT

An earplug for blocking sound and method of making the same, which includes a planar insert within an earplug of compressible slow recovery foam. A method of attenuating sound by inserting the earplug at an ear canal entry so that the planar insert is tactilely vertical, and pushing the earplug into the ear canal allowing the earplug to flex perpendicular to planar surfaces of the planar insert.

12 Claims, 15 Drawing Sheets

(56) References Cited

U.S. PATENT DOCUMENTS

| | | |
|---|---|---|
| 2004/0129276 A1 | 7/2004 | Kuno et al. |
| 2008/0276945 A1 | 11/2008 | Rosen |
| 2010/0095971 A1 | 4/2010 | Johnson et al. |
| 2010/0300460 A1* | 12/2010 | Falco .................... A61F 11/08 156/256 |
| 2012/0199143 A1 | 8/2012 | Turdjian et al. |
| 2013/0186415 A1 | 7/2013 | Falco |
| 2016/0302974 A1 | 10/2016 | Chenal |
| 2017/0026734 A1 | 1/2017 | Walker et al. |

OTHER PUBLICATIONS

"Compress" Merriam-Webster.com Dictionary, Merriam-Webster, https://www.merriam-webster.com/dictionary/compress. p. 2. (year: 2022).

"Flatten." Cambridge Dictionary, https://disctionary.cambridge.org/us/dictionary/english/flatten. p. 2. (Year: 2022).

Clifford Olson, "How to use Foam Hearing Protection and Ear Plugs Proper Insertion Technique YouTube Video from Applied Hearing Solutions", 2022.

International Searching Authority, "International Search Report and Written Opinion", From Application No. PCT/US2019/046079, Mailed Nov. 4, 2019, pp. 11.

European Patent Office, "Extended European Search Report", From Application No. 19852625.3, Dated Jul. 22, 2022, pp. 9.

\* cited by examiner

COMPRESSIBLE FIT EARPLUG WITH PLANAR INSERT

CROSS-REFERENCE TO RELATED APPLICATION

This is a divisional of U.S. Non-provisional application Ser. No. 16/107,434 filed on 21 Aug. 2018.

FIELD OF THE INVENTION

The present invention relates to earplugs for providing noise attenuation.

BACKGROUND OF THE INVENTION

Earplugs are used to protect a wearer's hearing in a noisy environment. Such earplugs typically have a front portion for tightly fitting in a person's ear canal to block noise, and a rear portion that serves as a handle to assist in inserting and extracting the earplug. A common type of earplug has an elongated body for insertion into the ear canal, where the body is formed from compressible and slowly-rebounding foam. Insertion of the earplug into the ear canal is facilitated by the wearer rolling the earplug (or a portion thereof) between fingers to a small diameter and then inserted into the ear canal and allowing it to expand while it lies within the ear canal. Such earplugs generally must be inserted to a minimum depth in order to effectively block the ear canal.

Earplugs formed from slowly-rebounding or slow recovery foam are known in the art. For example, U.S. Pat. No. 4,774,938 (the entire content being incorporated herein by reference) describes an earplug of the slow recovery type, which has open cells for expelling gas to the outside during compression, but which resists the entry of water through the outside and the soiling of the outside by dirt. U.S. Pat. No. Re. 29,487 (incorporated herein by reference) describes earplugs composed of foamed plasticized polymeric material having a sufficiently high concentration of plasticizer to provide the earplug with a reduced rate of recovery from compression. Earplugs formed with slow recovery foam are characterized by allowing a user to compress and manipulate the earplug foam material to a reduced size for fitting into the ear canal and then providing for expansion of the compressed foam after some short recovery period, but not immediately after removing the compressing force. This "short recovery period" allows the earplug to be inserted and positioned within an ear before the earplug expands.

One issue with these presently-available earplugs is that the earplug wearer may lack the manual dexterity to "roll" the earplug to obtain the desired compression of the earplug. That is, the user may be wearing gloves or have another limitation that prevents the earplug from being both compressed and rolled to allow insertion into an ear. Another issue is that, even if the earplug is properly "rolled", the insertion of the compressed earplug into the ear canal may result in the earplug being folded or distorted such that the earplug cannot be fully and correctly inserted into the ear. Finally, insertion of presently-available earplugs, even if fully inserted, may still result in a misalignment of the earplug such that the earplug after expansion does not result in a full contact fit to the ear canal. A full contact fit is desired, especially in industrial environments where sufficient noise attenuation provided by earplugs is required for a safe working environment. The industrial use of earplugs is closely regulated by the U.S. Government Federal Agency, OSHA which regulates the sound mitigating effectiveness and the requirement for supervision of correct and consistent wearing of earplugs in industrial context. The relevant population are workers in industrial context. This tends to have workers who have a wide range of dexterity and of patience with and tolerance for the requirement, and the regulations are aimed at that portion of the industrial population who are more likely to be less able or willing to take care for their protection. Therefore, there exists a need for compressible earplugs that require less dexterity and patience and provide for a higher level of assurance of proper alignment in the ear canal. One aspect of the regulations brings supervision into the process because the employer is responsible for adequate protection. The supervision issue is that an easily visible confirmation of proper insertion be available; for example, as a group of workers in a shift are inspected as they go into their work environment.

DETAILED DESCRIPTION OF THE PREFERRED EMBODIMENTS

The entire content of each of the following US Patents is incorporated herein by reference: U.S. Pat. Nos. 9,763,832; 6,345,684; 5,811,742; 6,006,857; 5,203,352; 4,774,938; 4,434,794 and Re. 29,487.

The present invention provides an earplug having a relatively rigid planar piece inserted into a deformable elongated body. The elongated body, also referred to herein as the earplug body, may be made of a compressible slow recovery polymeric foam that can be deformed into a compressed shape and which will expand by itself to fill the ear canal of a user after insertion into the ear canal. The slow recovery foam of the earplug body may be of the type described in U.S. Pat. Nos. 5,203,352 or 4,774,938 or U.S. Pat. No. Re. 29,487 (the entire content of each of them being incorporated herein by reference). The earplug body may be made of other compressible materials that provide the desired slow recovery characteristics. The elongated earplug body has a generally elongated shape with an outer surface being generally symmetric with respect to a center axis when in an uncompressed state. The elongated earplug body may also be tapered with a front end having a smaller cross-sectional area (commonly as a diameter) than a rear end, where the front end is inserted into the ear canal. In common embodiments the earplug body will have a circular cross-section along its length; however other configurations are possible.

Figure 7:
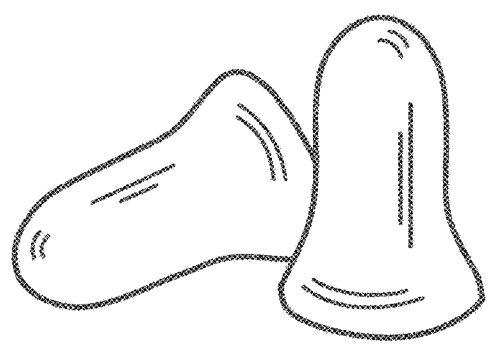
FIG. 7 shows a Howard Leight™ Max® bell shape earplug.
Figure 8:
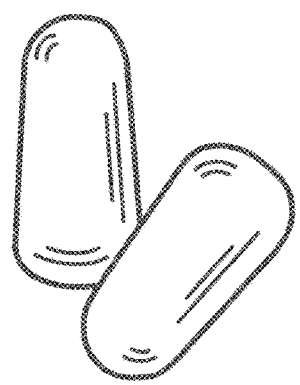
FIG. 8 shows a Honeywell Howard Leight™ X-TREME® earplug.

For convenience, but not in limitation of the invention, two well-known earplug designs are used as exemplary embodiments of earplugs for the present description. These designs are shown in FIG. 7 and FIG. 8. FIG. 7 shows an earplug design from Honeywell described as the Howard Leight™ Max® single use bell shape disposable uncorded earplug. The bell shape of the earplug being the distinguishing shape and its common nomenclature. The Max® earplug also comes in a corded version. FIG. 8 shows another earplug design from Honeywell described as the Howard Leight™ X-TREME® disposable earplug. The X-TREME® earplug is characterized by a tapered shape with the front end having a smaller diameter than the rear end; it can be referred to as a bullet shape. Another commercial earplug design which is relevant here is the Honeywell Howard Leight Laser Lite Earplug, which can be considered symmetrical for the present purposes.

The relatively rigid planar piece is also referred to herein as a planar insert. The planar insert is a generally flat element for the portion of the planar insert contained within the elongated earplug body. For the portion of the planar insert within the earplug body, the planar insert has a length along a center longitudinal axis and a height perpendicular to the center axis. The planar insert has a thickness defined by the distance between two oppositely facing planar sides for the portion of the planar insert within the earplug body, where the thickness is less than the length or height of the planar insert. The oppositely facing planar sides are generally parallel to the height and length dimensions of the planar insert and being parallel to each other, that is the planar insert is flat. It is considered that the planar sides being separated by the relatively thin thickness of the planar insert define a plane of the planar insert, The planar insert is made of a material with a rigidity greater than the rigidity of the material used for the earplug body. While there are technical qualities for rigidity and/or flexibility, it is in the function of the planar insert that its rigidity and flexibility can be defined. That function first appreciates that inserting a compressed foam plug has the problem that it is too soft for controlled insertion since it freely bends and otherwise distorts and compresses. The planar insert is stiff enough to keep the shape of the earplug upon insertion but flexible enough to bend in response to the shape of the ear canal and the inexactness of the positioning. The flexibility of the planar insert as defined herein includes the freedom to bend with resilience by a restoring force allowing it to self-adjust its shape during the insertion process. That flexibility is provided perpendicular to the planar surfaces. The planar insert is positioned inside the earplug body to allow the user to compress (also called flattening or pinching) the earplug parallel to the plane of the planar insert against each of the planar sides. Compressing the slow recovery material of the earplug results in the earplug having a flattened shaped cross-section (which can variously be referred to as "pinched" or "pinched shaped" or "compressed" or "flattened" all having the same intended meaning), where the compressed earplug has a thickness smaller than its height. This is distinguished from the conventional rolling of the compressible slow recovery earplug into a compressed rod or pin shape which gives no assistance to effective insertion, it is just smaller, but is easily distorted and easily badly inserted and has no match to the shape of the ear canal.

The flattened shape of the present description adapts well to insertion into the ear canal, since the ear canal at least at its entrance, is generally more oval-shaped than circularly-shaped, that is, it has a height that is greater than its width with anatomically smooth rounding defining the shape. As it is inserted into the ear canal, the flattened shape of the compressed earplug can rotate to some extent to better align itself to the shape of the ear canal, that is, it will self-align. The user may also detect a mispositioning or misalignment of the earplug within the ear canal due to tactile feed-back sensing of resistance during insertion and may manually rotate the earplug or hold it loosely so as to allow the self-alignment. That self aligning rotation will occur by itself as the earplug is pushed in because of the rigidity contributed by the planar insert which maintains the shape of the earplug in which the vertical dimension is established by the height of the planar insert and the horizontal dimension is determined by the flattening or pinching. Therefore the process of insertion begins, after the flattening step, with the user, by tactile sensitivity orienting the flattened earplug as best he can to the vertical orientation, placing it at the ear canal opening and then allowing, again by feel, any corrective tilting to have it most readily fit to the ear canal opening and then inserting, again by feel, into final position in the ear canal. This process is referred to as "tactile orientation and self-alignment" referring to the two steps, first the user putting it in position at the ear canal entrance with the best feeling for vertical orientation available to the user, and then allowing it to self-align to the correct orientation for entry into the ear canal as it is pushed into the ear canal.

Thus, the flattened shape of the compressed earplug and the rigidity of the earplug provided by the planar insert facilitate both the initial orientation in self-alignment and the detection and correction of the misalignment by tactile reaction at the ear canal entry and then by its self-adjustment by flexing horizontally to the internal shape of the ear canal. The rotation to the desired orientation of the earplug during insertion should result in a better fit of the earplug to the ear canal when the earplug recovers to provide more or full contact of the earplug to the ear canal. It also prevents the misshaping of the earplug during insertion as happens with prior earplugs that have no or insufficient structure to keep the shape, that shape in the present embodiment being maintained by the planar insert. The self-alignment perpendicular to the planar surfaces (thought of as horizontal flexibility) accompanied by the absence of flexibility in the vertical plane of the planar surfaces (thought of as vertical rigidity) thereby allows for the initial self-aligning positioning relative to the shape of the ear canal entrance and the self-adjustment by horizontal flexible adjustment to the shape of the ear canal as insertion commences. Thus, the planar insert provides such rigidity of the earplug shape to both provide guidance during insertion and prevent misshaping of the earplug as entering into the ear canal while still allowing such flexing as required by the ear canal shape. It is flexible enough to bend according to the shape of the ear canal. It is understood that the planar insert can bend in the direction of the plane (described as perpendicular to the planar surfaces) that is defined by its planar shape. Given that Young's modulus (also known as elastic modulus) is the measure of the stiffness of a material, the material of the planar insert will generally have a higher Young's modulus than the material of the earplug body containing the planar insert. More simply, the planar insert will typically have a higher elastic modulus than the earplug body so as to facilitate insertion of the earplug into an ear by providing a shape consistent with that of the era canal but also allowing flexing as consistent with the ear canal. The rigidity and flexibility as described is achieved by the planar insert being made of a plastic such as a PVC and being thin enough to allow the sideways (referred to as horizontal) flexibility. The range of flexibility can be understood as for its use, which is to allow flexing in the course of fitting into the ear canal of a range of users. The material of the planar insert is a resilient polymeric material. Having a Young's modulus of no more than 50,000 psi is suitable for the planar insert.

The earplug body may be fabricated with an internal space such as a slot extending lengthwise, to receive the planar insert and adhesives may be used to fasten the planar insert to the plug body after the planar insert is installed into the earplug body. Other fastening mechanisms may also be used to fasten the planar insert within the earplug body. Alternatively, the earplug body may be formed around the planar insert, where contact forces between the material of the earplug body and the planar insert hold the insert in place, or adhesives or other fastening mechanisms may be used to hold the insert in place. In embodiments described herein, the planar insert will have a portion extending past the rear end of the earplug to provide a handle for a user to hold and control it at the flattening step and the insertion step. The handle portion of the planar will also provide assistance for removing the earplug and also to allow visible determination that an earplug has been inserted such as during supervisory observation in the industrial context to meet OSHA requirements. Therefore, by holding the rearward extension in a position in which the user feels that the planar insert is vertically oriented, albeit imperfectly, and the earplug axis is generally horizontal, or in more human terms, being held so as to feel that it is correctly oriented for insertion, the flattened shape of the earplug is then close to matching the ear canal entrance, and any misalignment will tend to be corrected as the earplug is pushed into the ear canal. It is recognized that recovery of the earplug from the pinched or flattened state starts immediately, therefore the rigidity provided by the planar insert helps to quickly overcome the resulting misorientation, that can occur by the recovery as the insertion is done. For comfortable insertion, the earplug can be rocked up and down in very slight motion, and gently initially pushed in until it is sufficiently in that simple straight-in pushing finishes the insertion.

In the following description it is understood that looking at the earplug seeing the edge of the planar insert is a "top view" and looking at the earplug seeing the flat planar surface of the insert is a "side view".

Figure 1:
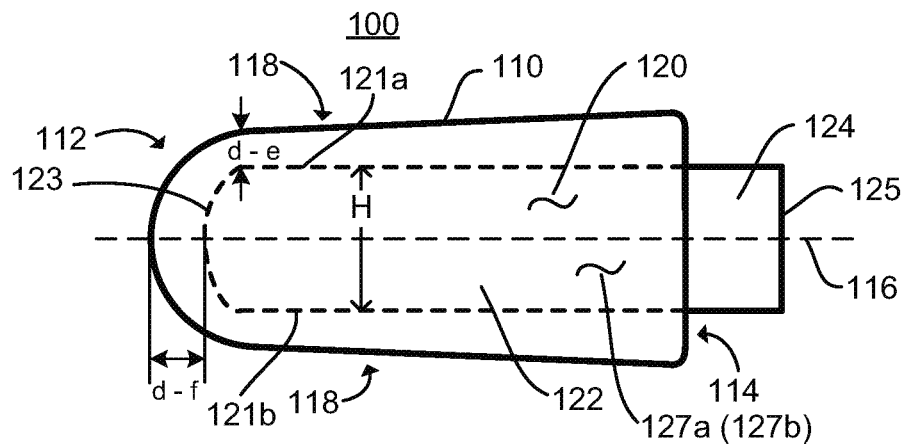
FIG. 1 shows a side view of a tapered cylindrically-shaped earplug in the uncompressed state with a planar insert.

FIG. 1 illustrates an earplug 100 of an embodiment of the present invention, which includes a planar insert 120 contained within an earplug body 110. In the illustrated embodiment the earplug body 110 has a generally tapered cylindrical shape with a curved forward termination 112, a planar rearward termination 114 that is generally perpendicular to a central axis 116 of the earplug body, and external surface 118 of circular cross-section that is tapered towards the central axis 116 from the rear toward the front. The earplug 100 depicted in FIG. 1 may be considered to have a shape similar to the Howard Leight™ X-TREME® disposable earplug shown in FIG. 8 commonly referred to as "bullet shaped".

Figure 2A:
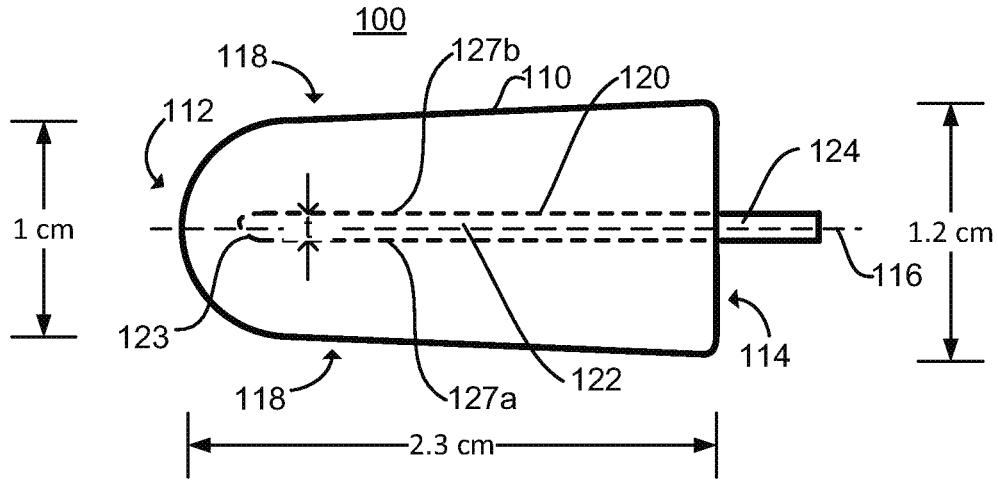
FIG. 2A shows a top view of the earplug of FIG. 1.

FIG. 2A shows a side view of the earplug 100 having the planar insert 120. In this embodiment, the planar insert 120 is of generally rectangular shape, extending along the length of central axis 116 and defined by parallel upper and lower edges 121a and 121b and oppositely facing planar surfaces 127a and 127b, a forward or front termination 123 and a rearward or rear termination 125. The forward termination 123 extends to near but at a selected minimum distance d-f back from the forward termination 112 of the earplug body 110. The edges 121a and 121b maintain a selected minimum distance the from the external surface 118 of the earplug body 110 The selected minimum distance d-f of the insert forward termination 112 and the selected minimum distance the of the edges 121a and 121b being selected to maintain sufficient foam body of the earplug body 110 between the insert and the user's ear canal to allow the earplug body to conform to the shape of the ear canal thereby providing the noise reduction to the ear and also to protect the ear canal from either or both injury and discomfort as might be caused by the insert 120 coming too close to the surface of the ear canal.

In FIG. 1, the planar insert 120 has a full length from the forward termination 123 to a rear end 125 and defining an internal planar insert portion 122 inside the earplug body 110. and an external portion 124 that projects rearward from the rearward termination 114 of the earplug body 110. The internal portion 122 of the insert 120 also extends symmetrically oriented along the central axis 116 towards the external surface 118 keeping the minimum distance d-e. While it is preferable that the external portion of the planar insertion be a matching planar shape of the internal planar portion, it can a different shape as may be desired.

Figure 9:
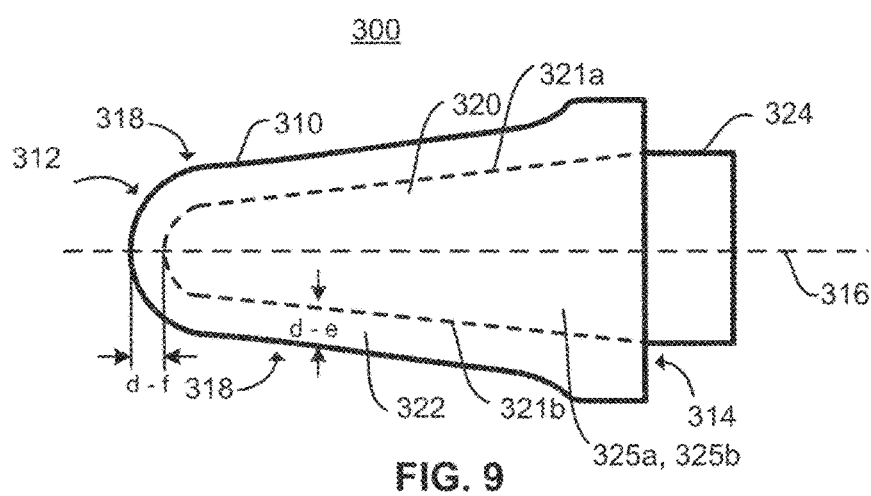
FIG. 9 shows a side view of a bell-shaped earplug with a planar insert.
Figure 10A:
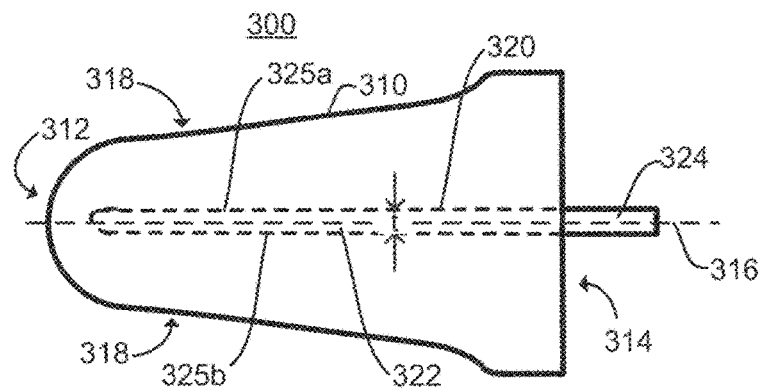
FIG. 10A shows a top view of the earplug of FIG. 9.
Figure 10B:
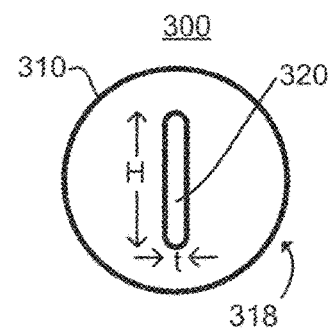
FIG. 10B shows a back view of the earplug of FIG. 9.

Hence, the planar insert 120 has a planar shape defined by parallel oppositely facing planar surfaces 127a and 127b separated by the thickness t and having a height, H, larger than its thickness, t; and in this definition, defining a plane through the center of its thickness, parallel with the parallel oppositely facing planar surfaces 127a and 127b. This then provides sufficient rigidity to affect the insertion assistance as described herein while allowing limited bending along its side dimension (that is bending sideways) thereby facilitating the convenient effective insertion into the ear canal. In the embodiment of FIGS. 1 and 2A while the earplug body 110 is tapered, the insert 120 is not tapered. However, embodiments in which the insert is tapered are additional exemplary embodiments as will be described below. In such a further exemplary embodiment as shown in FIGS. 9, 10A and 10B (with the bell shaped exemplary earplug) the insert 120 is tapered to maintain its upper and lower edges being a constant distance from the surface of the earplug body which is desirable because it keeps a constant volume of foam above and below the insert upper and lower edges. In other exemplary embodiments the height of the planar insert may decrease toward the forward end so as to provide increasing distance of the foam to the surface of the earplug body.

Figure 2B:
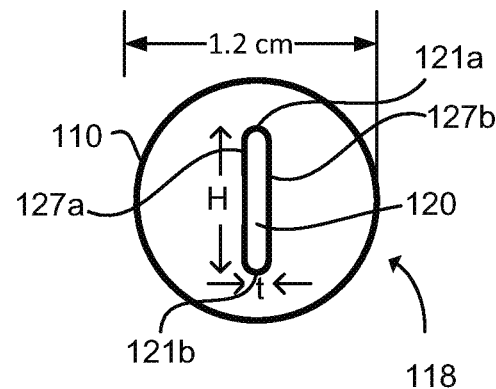
FIG. 2B shows a back view of the earplug of FIG. 1.

FIG. 2A illustrates a top view of the tapered cylindrical earplug 100 of FIG. 1. FIG. 2A shows the planar insert 120, having a thickness, t, disposed within the earplug body 110, where the planar insert 120 extends generally symmetrically along the central axis 116. The view shown in FIG. 2A illustrates the earplug 100 in an uncompressed state. In its uncompressed state, the top view of the earplug 100 illustrates that the curved forward termination 112, the rearward termination 114, and the external surface 118 generally have the same size and shape as that shown in the top view in FIG. 1. FIG. 2A shows the planar insert 120 having the internal portion 122 within the earplug body 110 and the external insert portion 124 that projects rearwardly from the rearward termination 114. FIG. 2B illustrates a back view of the uncompressed earplug 100. As shown in FIG. 2B, the planar insert 120 is disposed generally in the center of the earplug body 110 with a height, H, and a thickness, t. The cross-sectional shape of the earplug body 110 is generally circular, as defined by the external surface 118 tapering in circular cross-section. Dimensions are shown in FIGS. 2A and 2B, that are a length of about 2.3 cm and a diameter of about 1.2 cm which are typical dimensions of a commercial version of the bullet shaped earplug.

In the earplug 100 depicted in FIGS. 1, 2A and 2B, exemplary dimensions are a thickness, t, of about 1/64 to 1/32 inch and a height, H, of about 1/8 to 1/4 inch. Further, the minimum distance d-e from the external surface is not less than 20% of the diameter of the earplug body and is preferably at least 25% of the diameter. Also, the minimum distance d-f between the end of the planar insert and the end of the earplug body should not be less than 1/8 inch and not more than 1/4 inch, and preferably about 3/16 inch. Other embodiments of the earplugs described herein preferably have similar dimensions to allow for easy insertion of the described earplugs and retention of the earplugs inserted into an ear canal with sufficient distance of the planar insert from the surface of the earplug body to provide comfortable fit.

Figure 3A:
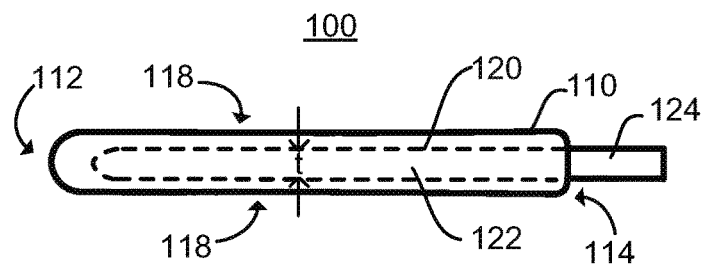
FIG. 3A shows a top view of the tapered cylindrically-shaped earplug in a compressed state.
Figure 3B:
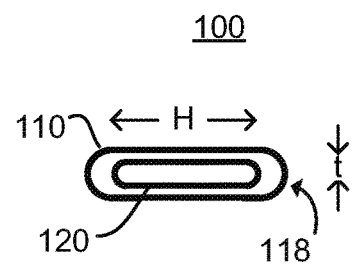
FIG. 3B shows a back view of the tapered cylindrically-shaped earplug in a compressed state.

FIG. 3A illustrates a top view of the earplug 100 in a compressed state, i.e., after the earplug body 100 is compressed (or pinched or flattened) prior to its insertion into an ear canal. As shown in FIG. 3A, the thickness, t, of the planar insert 120 stays the same after compression of the earplug body 120 due to it having a resistance to compression in this context. However, the overall dimension of the earplug body 110 in the direction perpendicular to the plane of the planar insert 120 is decreased into the compressed shape, Pinching of the earplug body 110 will cause the curved forward termination 112, the planar rearward termination 114, and the external surface 118 to all deform into the flattened shape, although the amount of dimensional decrease for and across each portion 112, 114 and surfaces 118 may differ due to the personal manner and exactness of the pinching action by the various users when done by hand. This is more exactly controlled when done by a mechanism as described below. FIG. 3B illustrates a back view of the compressed earplug 100. As shown in FIG. 3B, the insert 120 is still disposed generally in the center of the earplug body 110 with its height, and thickness, t. However, after compression, the general shape of the earplug body 110 is the flattened shape as defined by the external surface 118 being flat and generally parallel with the adjacent oppositely facing planar surfaces of the insert 120. As discussed above, this flattened shape facilities an easier insertion of the earplug 100 into the ear canal and also facilitates a better fit of the earplug 100 in the ear canal after insertion.

Figure 4A:
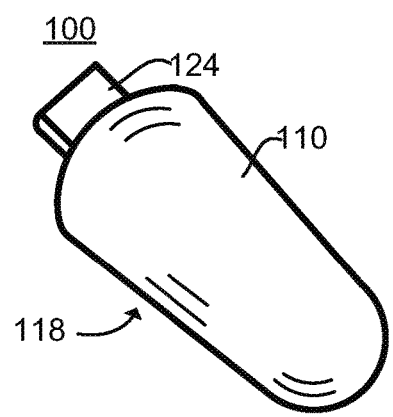
FIG. 4A shows a forward perspective view of the earplug showing the overall tapered cylindrical shape of the earplug body in the uncompressed state.
Figure 4B:
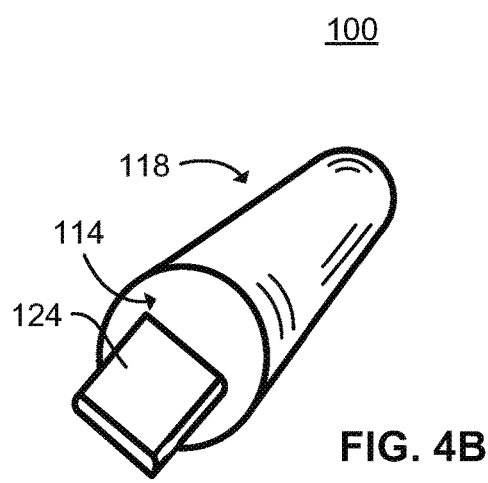
FIG. 4B shows a rearward perspective view of the tapered cylindrically-shaped earplug in the uncompressed state.

FIG. 4A illustrates a forward perspective view of the uncompressed earplug 100, showing the overall cylindrical shape of the earplug body 110 as defined by its external surface 118. FIG. 4A also shows the external insert portion 124 that projects rearward from the earplug body 110. FIG. 4B illustrates a rearward perspective view of the uncompressed earplug 100 having a tapered cylindrical shape defined by the external surface 118. FIG. 4B further shows the external insert portion 124 that projects rearward from the rearward portion 114 of the earplug body 110.

Figure 5A:
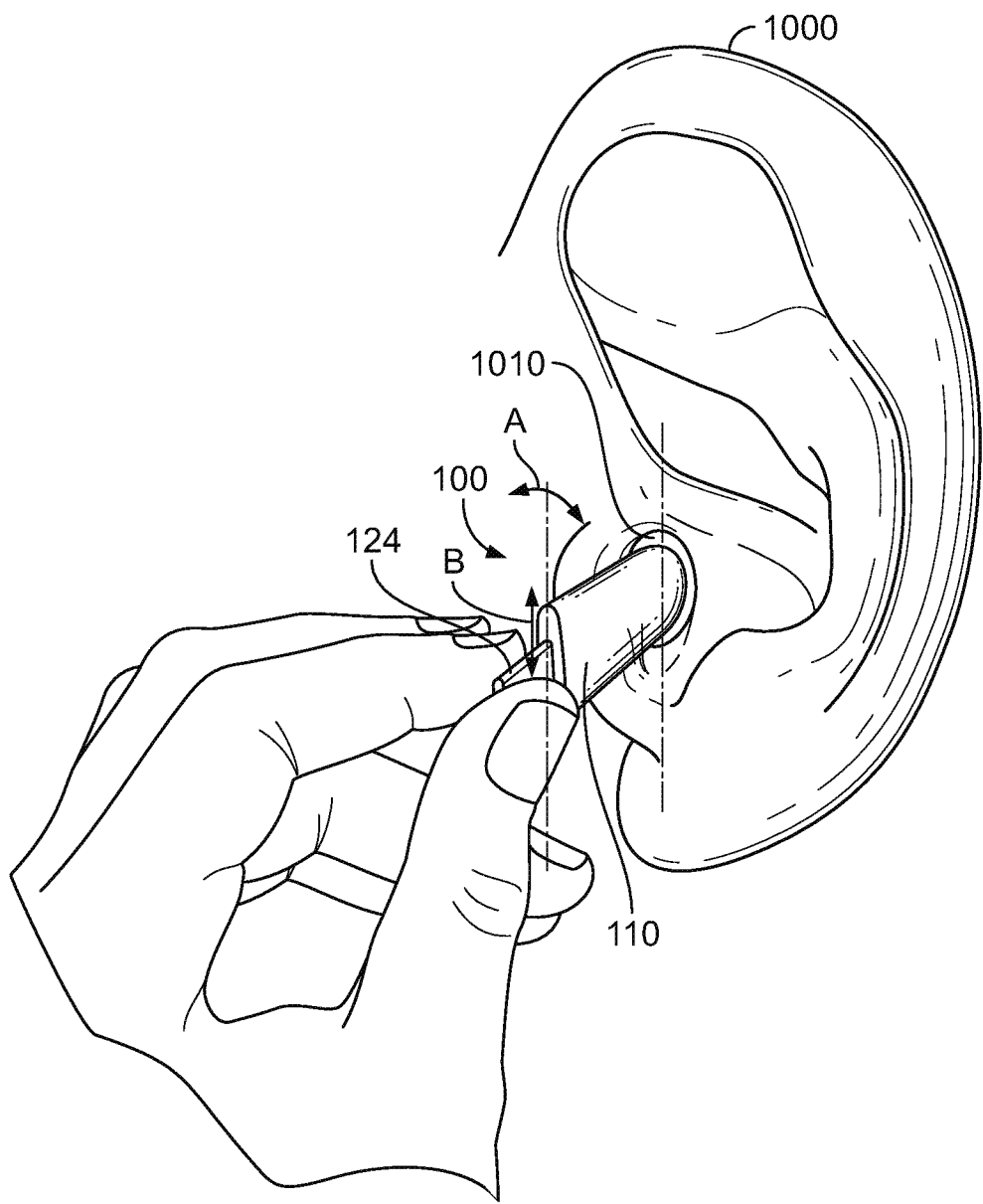
FIG. 5A shows an earplug in a compressed state at the initial state of insertion.

FIG. 5A illustrates the earplug 100 after being compressed and being ready for insertion into an ear canal 1010 of an ear 1000. As shown in FIG. 5A, the earplug body 110 has the generally flattened cross-section as seen in FIGS. 3A and 3B. FIG. 5A also shows the external insert portion 124 which may be gripped or pushed to facilitate insertion of the earplug 100 into the ear canal 1010. As seen in FIG. 5A, the earplug 100 is oriented in what will be termed a tactile vertical orientation, meaning how the user starts with a considered vertical orientation, but which is generally a user's tactile approximation to vertical. That approximation is sufficient given the flattening of the earplug 100 and the generally vertically oriented dimension of the ear canal opening that pushing the earplug 100 inward to the ear canal will self-adjust the orientation to a comfortable fit by the process of self-alignment coupled with the feel of comfortable insertion. That adjustment is depicted by arrow A. Also, as is noted above the advantageous process of initially gently rocking the earplug up and down until a good fit is felt can be used as depicted by arrow B.

Figure 5B:
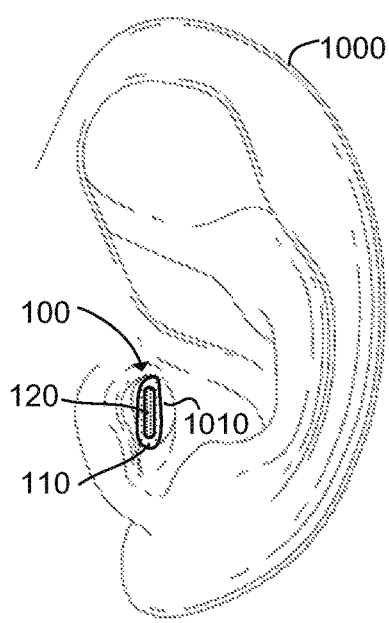
FIG. 5B illustrates the inserted tapered cylindrically-shaped earplug in a compressed state inserted in the ear canal of the ear while still compressed.
Figure 5C:
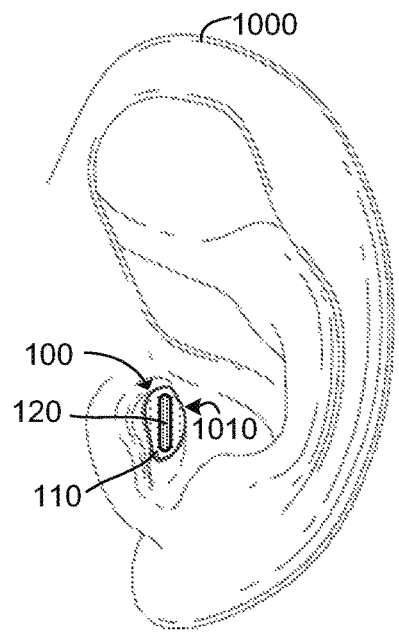
FIG. 5C illustrates the earplug within the ear canal after the earplug has expanded by slow recovery.

FIG. 5B illustrates the earplug 100 in its compressed state after insertion into the ear canal 1010 of the ear 1000. As shown in FIG. 5B, the earplug body 110 is compressed, so the earplug 100 has the flattened shape (similar to the shape depicted in FIGS. 3A and 3B). The entrance of the ear canal 1010 normally has a generally oval shape, so the compressed earplug 100 as being inserted will tend to rotate as may be needed to better align its flattened shape with the oval shaped entrance to the ear canal 1010 in which the height dimension of the insert 120 will align with the longer vertical dimension of the oval shaped ear canal 1010, This rotation allows for the earplug 100 to be more easily inserted into the ear canal 1010 and result in a better and more consistently occurring fit of the earplug 100 within the ear canal 1010 over a large population of industrial users. FIG. 5C illustrates the earplug 100 within the ear canal 1010 after the earplug has done its slow recovery. As shown in FIG. 5C, the earplug 100 has expanded to match the overall oval shape of the ear canal 1010 and is in contact with the wall of the ear canal 1010. The earplug 100 has not expanded to its original circular cross-sectional shape (as shown in FIG. 3A). Rather, the earplug 100 has expanded to fit the contour of the ear canal 1010, which will result in a good fit of the earplug 100 within the ear canal, which will result in the desired sound attenuation to be provided by the earplug. It is understood that recovery of the compressed earplug begins immediately when the pinching action is released, and therefore the insertion must take place quickly; but if there is any resulting difficulty, the compressing can be easily repeated, and repeated insertion attempt can be accomplished.

Figure 6A:
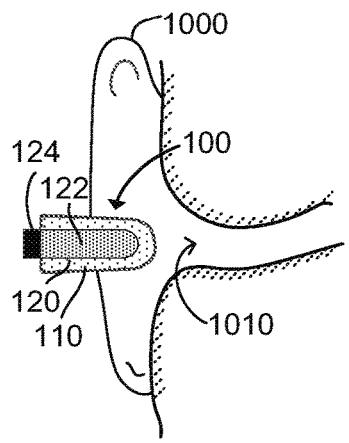
FIG. 6A shows a side view of the ear canal with an earplug in a compressed state positioned at ready for insertion into the ear canal.
Figure 6B:
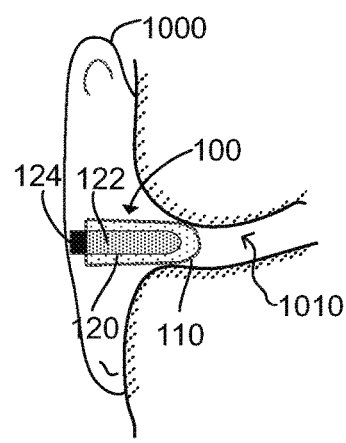
FIG. 6B shows the compressed earplug being at the initial state of insertion into the ear canal.
Figure 6C:
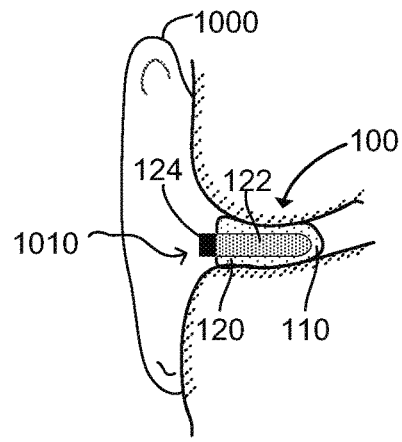
FIG. 6C shows the earplug fully inserted within the ear canal alter the expansion of the earplug.

FIGS. 6A-6C further illustrate the insertion of the earplug 100 into the ear canal 1010 of the ear 1000. FIG. 6A shows a side view of the ear canal 1010 with a side view of the earplug 100 in the compressed state positioned ready for insertion into the ear canal 1010. FIG. 6B shows the compressed earplug 100 being positioned at the entry of the ear canal 1010. FIG. 6C shows the earplug 100 fully inserted within the ear canal 1010 after the recovery of the earplug 100. As shown in FIG. 6C, the earplug body 110 essentially conforms to and is in contact with the contours of the ear canal 1010 after expanding within the ear canal. However, the rigid insert 120 within the earplug body 110 generally retains its original vertical shape even after expansion of the earplug body 110. The expansion of the earplug body 110 within the ear canal 1010 results in a tight fit of the external surface in contact with the ear canal which will provide the desired sound attenuation. The insert and the earplug body have been dimensioned such that there will be sufficient foam of the earplug body 110 between the insert internal portion 122 and the ear canal to not have any contact with the ear canal and to avoid discomfort from the insert internal portion 122.

Figure 6D:
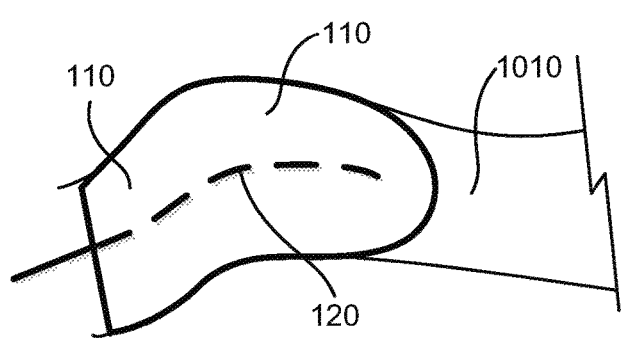
FIG. 6D schematically shows an ear canal as viewed on a horizontal plane with an exemplary insertion of the earplug in the ear canal.

FIG. 6D is a schematic illustration on a horizontal plane showing the ear canal with an earplug 100 fully inserted and recovered such that the earplug body 110 has readily conformed to the shape of the ear canal 1010, while in this exemplar, the planar insert 120 functioning in cooperation with the earplug body 110, has undergone a minor horizontal flexing thereby accommodating both minor and major curvatures of the ear canal 1010. This minor flexing of the planar insert allows the earplug to fully conform to the shape of the earplug canal and facilitates the retention of the earplug within the ear canal.

Other embodiments of the present invention may have earplug bodies having different shapes than that illustrated in FIGS. 1 through 4B. As briefly noted above, the present invention is not limited to a tapered cylindrically shaped earplug body, a curved forward portion or a planar rearward portion. Similarly, the planar insert is not limited to a generally rectangular shape.

FIG. 9 illustrates an earplug 300 according to another embodiment of the present invention. The earplug 300 includes a tapered planar insert 320 contained within a bell shape earplug body 310 and having parallel oppositely facing planar surfaces 325a and 325b. The bell shape earplug body 310 has a curved forward termination 312, a flat rearward termination 314 that is generally perpendicular to a central axis 316 of the earplug body 310, and external surface 318 that slopes towards the central axis 316 in a tapered fashion of circular cross-section from the rearward portion 314 to the forward portion 312. The illustrated earplug body 310 for exemplary purpose replicates the shape of the commercial bell shaped earplug as described above and in FIG. 7. FIG. 9 shows a side view of the earplug 300. In FIG. 9, an internal insert portion 322 of the tapered insert 320 extends along the length of the central axis 316, but does not extend all the way to the front of the forward portion 312 of the body 310 leaving as described above a selected distance d-f. The taper as illustrated has edges 321a and 321b that extend in parallel with the surface 318, that is they are a constant distance from the surface 318, that distance being a selected distance d-e as discussed above. The insert 320 also has an external insert portion 324 that projects rearward from the rearward termination 314 of the earplug body 310 defining a handle. FIG. 10A illustrates a top view of the bell-shaped earplug 300. FIG. 10A shows the insert 320, having a thickness, t, between the oppositely facing planar surfaces 325a and 325h, disposed within the earplug body 310, where the insert 320 is generally disposed symmetrically around the central axis 316. The view shown in FIGS. 9 and 10A and 10B illustrate the earplug 300 in an uncompressed state. In its uncompressed state, the top view, FIG. 10A of the earplug 300 illustrates that the curved forward termination 312, the planar rearward termination 314, and the external surface 318 generally have the same size and shape as that shown in the side view in FIG. 9, the shape being generally circular in cross-section. FIG. 10A shows the insert 320 having the internal portion 322 within the earplug body 310 and the external insert portion 324 that projects rearwardly from the planar rearward portion 314. FIG. 10B illustrates a back view of the uncompressed earplug 300. As shown in FIG. 10B, the insert 320 is disposed generally in the center of the earplug body 310 with a height, H, and a thickness, t. The general shape of the earplug body 310 is a tapered cone of circular cross-section as defined by the external surface 318.

Figure 11A:
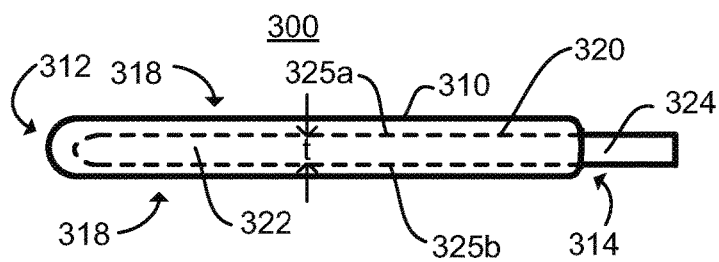
FIG. 11A shows a side view of the bell-shaped earplug in a compressed state.
Figure 11B:
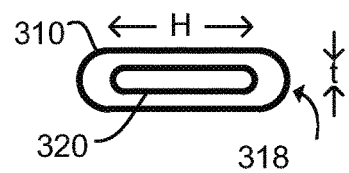
FIG. 11B shows a back view of the bell-shaped earplug in a compressed state.

FIG. 11A illustrates a top view of the earplug 300 in a compressed state, i.e., after the earplug body 300 is flattened or pinched prior to its insertion into an ear canal. As shown in FIG. 11A, the thickness, t, of the insert 320 generally stays the same after compression of the earplug body 310 due to the rigidity of the insert 320. However, the overall height of the earplug body 310 in the direction perpendicular to the plane of the insert 320 is decreased. Flattening of the earplug body 310 may cause the heights of the curved forward portion 312, the planar rearward portion 314, and the external surfaces 318 to all decrease, giving the flattened configuration. FIG. 11B illustrates a back view of the compressed earplug 300. As shown in FIG. 11B, the insert 320 is still disposed generally in the center of the earplug body 310 with a height, and a thickness, t. However, after compression, the cross-sectional (i.e., the cross-section perpendicular to the axis 316 shown in FIG. 11A) shape of the earplug body 310 is flattened, as defined by the external surface 318 such that it is substantially parallel on each side to its adjacent planar surface 325a and 325h of the planar insert 320. As discussed above, this flattened shape facilities an easier insertion of the earplug 300 into the ear canal and also facilitates a better fit of the earplug 300 in the ear canal after the earplug body 310 expands.

Figure 12A:
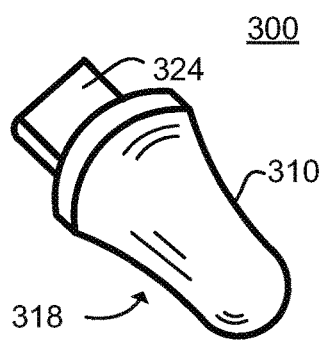
FIG. 12A shows a forward perspective view of the uncompressed earplug showing the overall bell-shape of the earplug body.
Figure 12B:
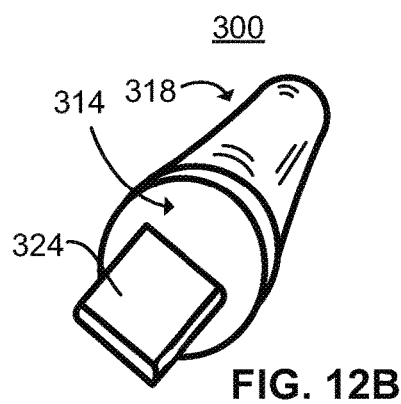
FIG. 12B shows a rearward perspective view of the uncompressed bell-shaped earplug.

FIG. 12A illustrates a forward perspective view of the uncompressed earplug 300, showing the bell shape of the earplug body 310 as defined by its external surface 318. FIG. 12A also shows the external insert portion 324 that projects rearward from the earplug body 310. FIG. 12B illustrates a rearward perspective view of the uncompressed earplug 300 having a bell shape defined by the external surface 318. FIG. 12B further shows the external insert portion 324 that projects rearward from the rearward portion 314 of the earplug body 310.

Figure 13:
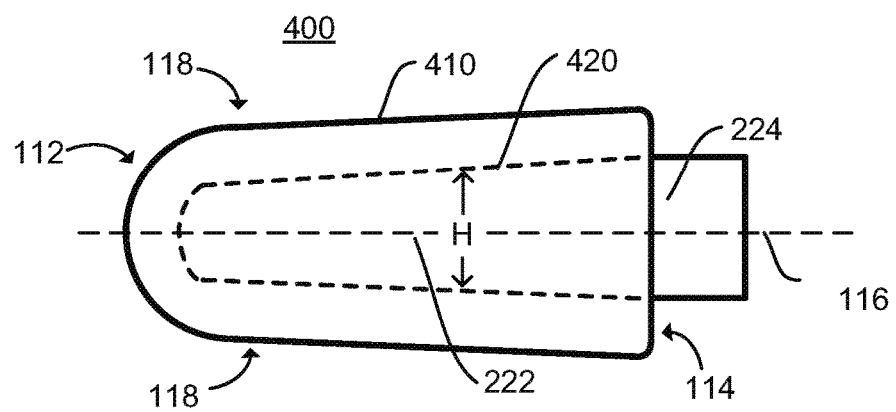
FIG. 13 illustrates a side view of a tapered earplug with a tapered planar insert that is not parallel to the outer surface of the earplug.

As briefly mentioned above, the planar insert according to the present invention may have various shapes. For example, FIG. 13 illustrates a side view of an earplug 400 with a tapered insert 420 but not, as in the embodiment of FIG. 9, parallel with the surface 410. The insert 420 is still generally disposed symmetrically around the center axis 116, but the height of the tapered insert 420 decreases towards the forward termination 112 of the earplug body 110, in this embodiment of such taper that its distance to the surface increases toward the front. Note that FIG. 13 shows a side view of the earplug 400. Top and back views of the uncompressed earplug 400 would be similar to that depicted in FIGS. 2A and 2B and of the compressed earplug would be similar to that shown in FIGS. 3A and 3B. Inserts of other shapes and other relationships to the earplug body may be used in accordance with embodiments of the present invention.

As briefly discussed above, the insert may be glued or otherwise fastened within the earplug body in a slot made in it, or the earplug body may be formed in the molding process around the insert to provide for adherence between the earplug body and the insert. Inserts of other shapes and other relationships to the earplug body may be used in accordance with embodiments of the present invention. However, the insert may also have additional features to provide for better fastening between the earplug body and the insert. It is therefore understood that the symmetrical positioning of the planar insert in the earplug and associated dimensions would be subject to tolerances incurred with the manufacturing process.

Figure 14:
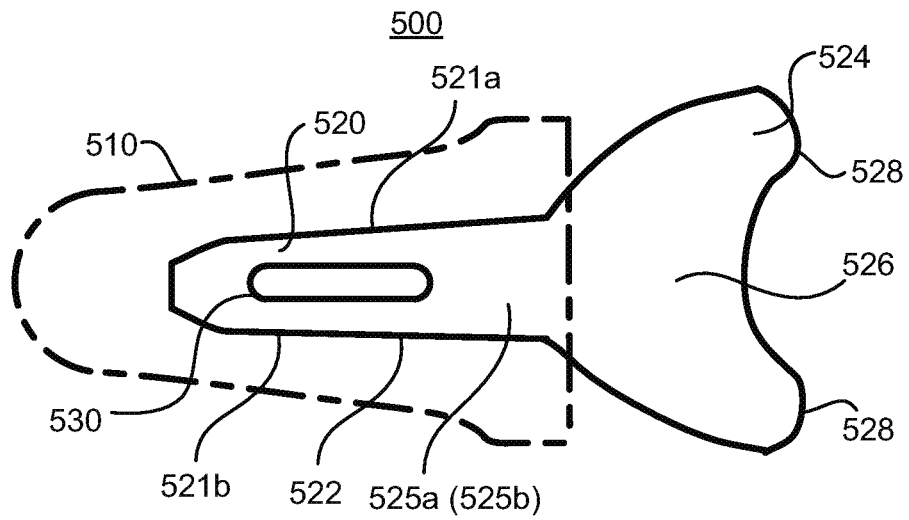
FIG. 14 illustrates a side view of a bell-shaped earplug with a tapered planar insert having a slot in an internal portion of the planar insert.

Such an additional feature is shown in FIG. 14 in which the configuration of the earplug of FIG. 9 (shown in phantom) is used as an exemplary embodiment, now designated as earplug 500 having an earplug body 510 (shown in phantom). The planar insert 520 has an internal portion 522 and an external portion 524. As is common with the prior described planar inserts it is a thin relatively rigid (relative to the foam earplug body) elongated form having edges 521a and 521b and oppositely facing planar surfaces 525a and 525b. The additional feature is the slot 530 in the internal portion 522 of the insert 522. The slot 530 provides for additional fixing of the planar inset 520 in the earplug body 510. In a manufacturing mode in which the insert is positioned in a mold and the foamable uncured plastic ingredients are poured around it, the foamed earplug body 510 will extend across the slot 530 fixing it in place. Alternatively, if the manufacturing procedure has the insert being inserted into a prepared slot in the foamed body, glue can be used, and it will fill across the slot 530 to provide the insert being fixed to the foam body. The slot 530 can be implemented in any form which the insert can have such as the embodiments as disclosed herein. The exemplary slot 530 has a length that is about ½ the total length of the internal portion 522 of the insert; although a length of the slot 530 can be in the range from about ¾ to about ¼ of the length of the interior portion of the insert. It is also seen that the external portion 524 has an exemplary shape having a solid body 526 extending on either side of which are lobes 528 thereby allowing for a larger gripping surface.

Figure 15A:
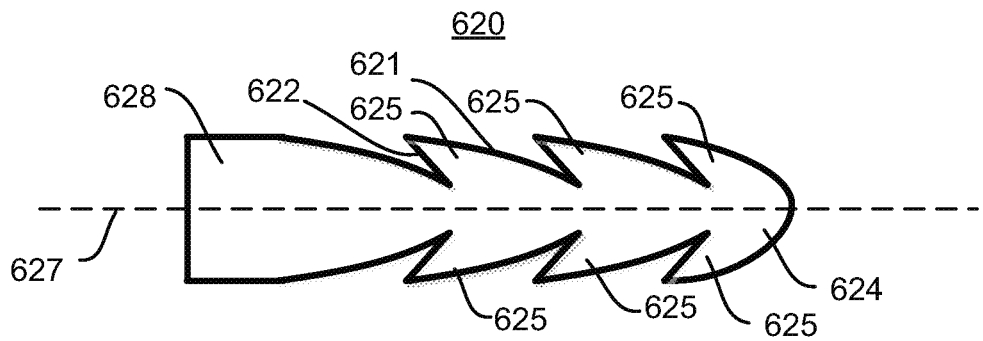
FIG. 15A illustrates a side view of a barbed planar insert.

FIG. 15A illustrates a side view of an insert 620 with additional features that facilitate better fastening of the insert 620 to an earplug body. Insert 620 is a planar insert having a forward termination 624, a number of barbs 625 projecting outwardly from a central axis 627 of the insert 620 and away from the forward termination 624, and an external portion 628 opposite the forward termination 624, As shown in FIG. 15A, the barbs 625 are generally shaped to provide a rearward pointing barb tip 622.

Figure 15B:
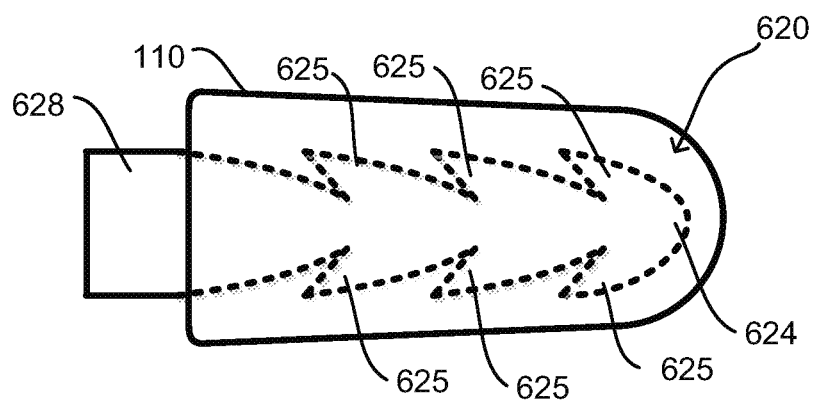
FIG. 15B illustrates the disposition of a barbed planar insert within an earplug body.

FIG. 15B illustrates the disposition of the barbed insert 620 as shown in FIG. 15A within an earplug body 110, similar to that shown in FIG. 1. As shown in FIG. 15B, the external portion 628 of the insert 620 projects rearward from the earplug body 110, while the barbs 525 are retained within the earplug body. A top view of the barbed insert 620 would be similar to that shown in FIG. 2A, since the barbed insert 620 is a planar insert having a height larger than its thickness being similar to the above described inserts with the barbs set into it. This planar configuration of the insert 620 facilitates the compression of the earplug body 110 prior to its insertion into an ear canal and expansion after insertion as described above in regard to other exemplary planar inserts.

The earplug body 110 depicted in FIG. 15B may be formed around the barbed insert 620 or the earplug body 110 may be formed with a feature to receive the barbed insert 620. This feature may comprise a slot, slit, or cavity (not shown) formed within the earplug body shown in FIG. 15B, The barbed insert 620 is then pressed into this slot slit, or cavity. The forward edge 621 of each barb 625 facilitates the insertion of the insert 620 due to the tapered shape of the forward edge 621. The retention of the insert 620 within the earplug body 110 is facilitated by the tip 622 of each barb resisting any backward movement of the insert 620 within the earplug body 110. It can be understood that using the barbed structure can allow insertion of the insert into the earplug body without any particular retaining element such as glue, and the barb then allows the earplug to be withdrawn, keeping in mind that the earplugs are intended for only a single use, so any partial disconnection of the insert from the earplug body is irrelevant.

Figure 16A:
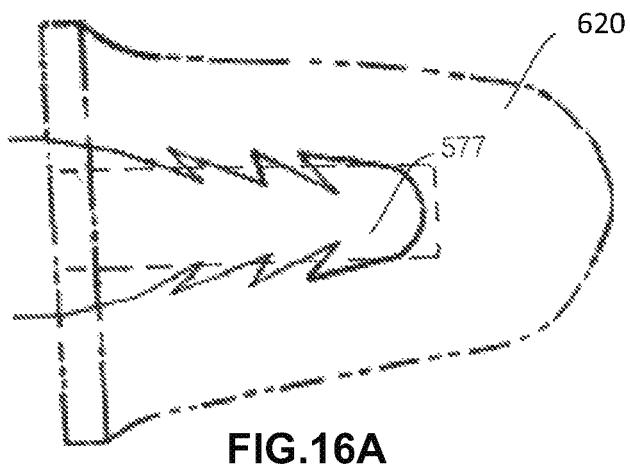
FIG. 16A shows a barbed planar insert with a generally constant height within a bell-shaped earplug.
Figure 16B:
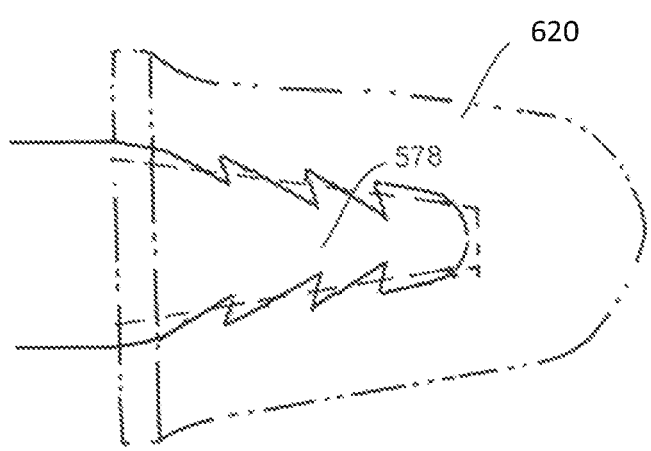
FIG. 16B shows a tapered barbed planar insert within a bell-shaped earplug.

FIGS. 16A and 16B show configurations of an earplug 600 having a barbed insert inside the earplug body 620 (shown in phantom) as from FIG. 9, In FIG. 16A the barbed insert 577 is of straight length while in FIG. 16B the barbed insert 578 is tapered. The barbs are in planar alignment with the insert 577.

Figure 17A:
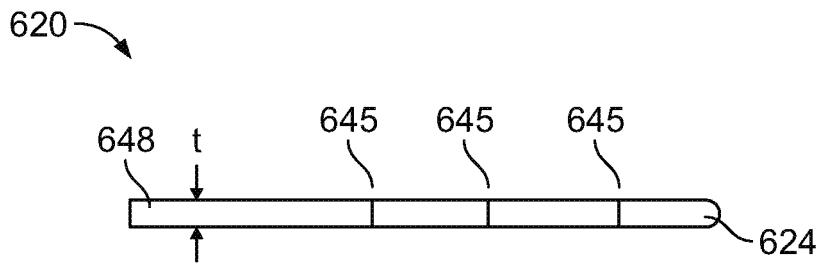
FIG. 17A illustrates a top view of a barbed planar insert.
Figure 17B:
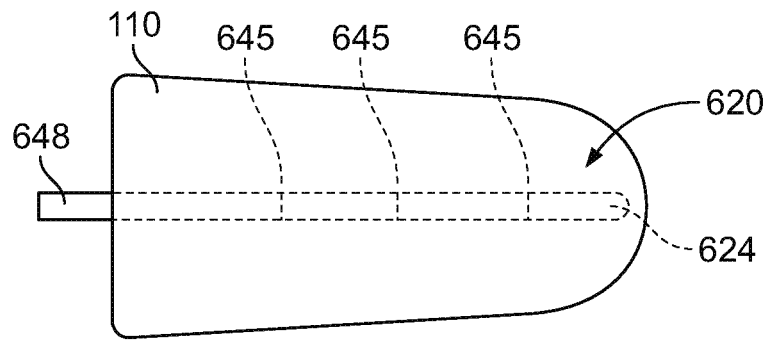
FIG. 17B illustrates a disposition of the barbed planar insert within an earplug body.

FIG. 17A illustrates a top view of the insert 620 of FIG. 16A and FIG. 17B show a top view of FIG. 16B.

Figure 18A:
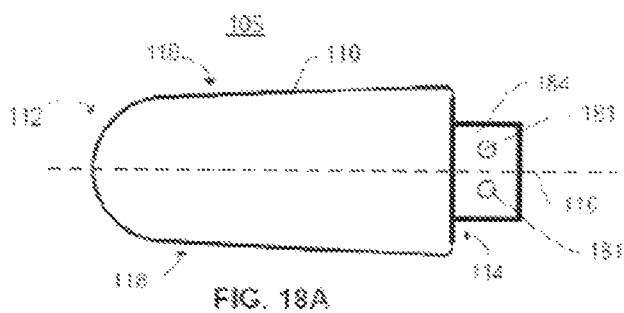
FIG. 18A depicts a planar insert disposed within a tapered cylindrically-shaped earplug body, where the planar insert has circular holes within an external portion of the insert.

Inserts according to the present invention may have additional features that may serve as anchor points for a wire or string. For example, FIG. 18A shows a side view of an earplug 105 similar to the earplug 100 shown in FIG. 1. In FIG. 18A, the earplug 105 comprises an insert disposed (not shown) within the earplug body 110. The insert has an external insert portion 184 that projects rearward from the rearward termination 114 of the earplug body 110. The external insert portion 184 has two holes 181 disposed parallel to the planar rearward portion 114 of the earplug body 110. The holes 181 may act as anchoring or tie-down points on the insert 180 for a wire or string such as used to join a pair of earplugs for convenience. It can be made with a single hole as well.

Figure 18B:
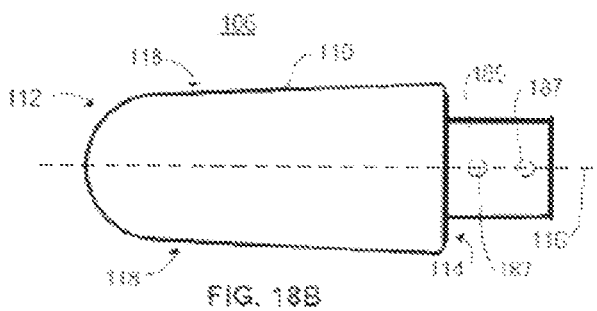
FIG. 18B depicts a planar insert disposed within a tapered cylindrically-shaped earplug body, where the planar insert has hexagonal holes within an external portion of the planar insert.

The holes 181 appear in FIG. 18A as circular cutouts aligned perpendicular to and on either side of the center axis 116 but may alternatively be any other two-dimensional shape located on any other area of the external insert portion 184. For example, FIG. 18B depicts an insert having an external insert portion 185 with hexagonally-shaped holes 187. The hexagonal holes 187 are disposed along the center axis 116 of the earplug 106. The number of holes disposed within the external portion may be more or less than the two depicted in FIGS. 18A and 18B. This type of hole is available to create corded versions of the earplug embodiments described herein.

Figure 18C:
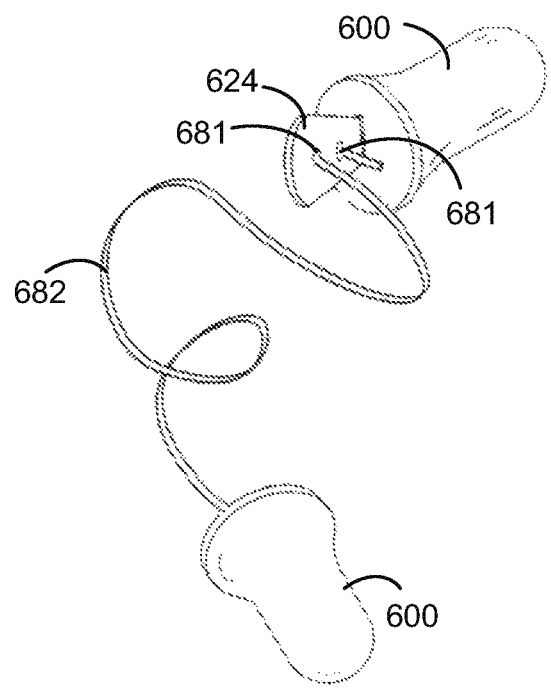
FIG. 18C shows an embodiment of earplugs joined by a cord.

FIG. 18C shows earplugs 600 having exterior portion 621 with holes 681 to which are attached wire or string 682; for use as known in the art.

As can be appreciated by the example of FIG. 14, the external portion of the insert according to the present invention is not limited to the rectangular shape and may also be formed with varieties of selected shape Further, the external portion of the insert may be formed so that it does not lie entirely in the plane of the insert.

As briefly discussed above, the planar insert variations described above and depicted in FIGS. 1 to 18B may be disposed within earplug bodies having the shapes described herein and other shapes that allow compression of the earplug body against at least some portion of the planar insert. The planar shape of the insert may also vary from the specific variations described herein.

Figure 19:
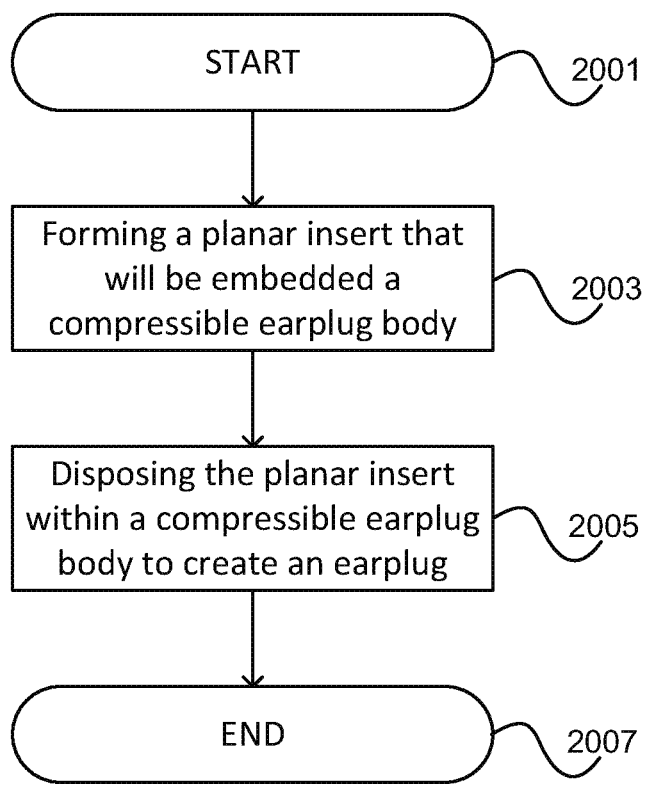
FIG. 19 illustrates the method of creating an earplug by combining a planar insert with an earplug body.

FIG. 19 illustrates steps of a method of creating an earplug having a planar insert. First, the planar insert is formed as part of step 2003. The planar insert may be formed as a plastic material using commonly-understood processes for the formation of plastic parts. The planar insert may also be formed with other materials that allow the creation of a part with a rigidity greater than that of material used to form an earplug body while having a resilient flexibility perpendicular to the planar surfaces. Next, the planar insert is disposed as least partially within an earplug body as part of step 2005. As discussed briefly above, the earplug body may be formed around the planar insert to form the earplug. Alternatively, the planar insert may be inserted into the earplug body to form the earplug. The earplug body may be formed from deformable elastomeric slow recovery foam or other material that allows for the compression of the earplug body and then the expansion of the earplug body generally to its original shape after a recovery period.

Figure 20:
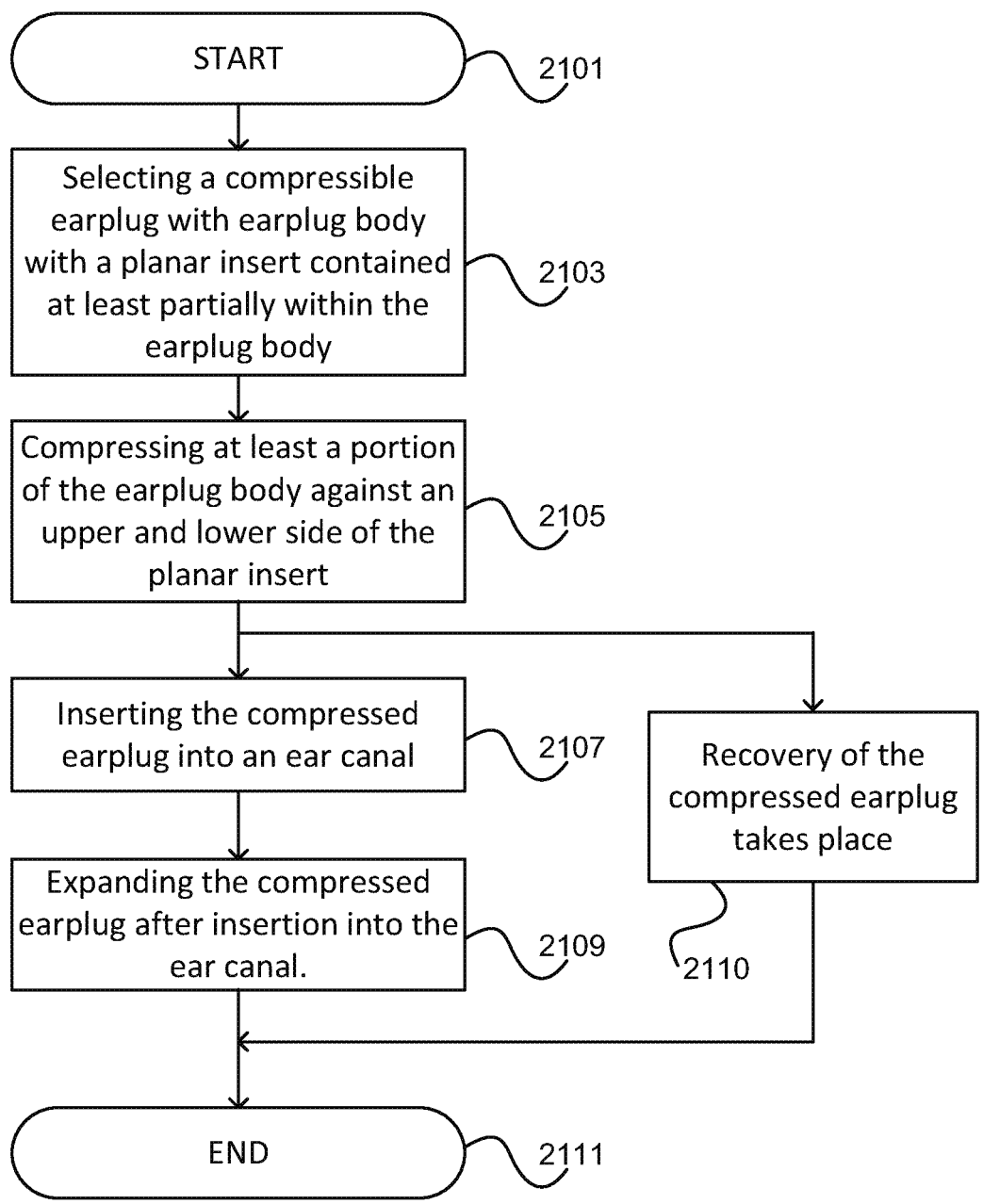
FIG. 20 illustrates a method for providing sound attenuation with a compressible earplug.

FIG. 20 illustrates a method for providing sound attenuation with a compressible earplug. First a compressible earplug is selected that has a planar insert as part of step 2103. The compressible earplug with a planar insert preferably comprises earplugs discussed above in reference to FIGS. 1 to 18B. The planar insert is contained within a compressible earplug body as described above for the various embodiments. The compressible earplug body and the planar insert may be selected separately, where the planar insert is inserted into the earplug body upon selection. Alternatively, the compressible earplug body may already contain the planar insert upon selection. The planar insert has a height and length greater than its thickness. The material of the planar insert has a greater rigidity than the material of the compressible earplug while having flexible resiliency perpendicular to the oppositely facing planar surfaces. Next, as shown in step 2105, the earplug body is compressed (flattened) against at least a portion of the oppositely facing planar sides of the planar insert within the earplug body to form a compressed earplug. This compression may be accomplished by the user gripping at least a portion of the earplug body with the user's thumb and forefinger (or another finger of the user's hand) and pressing the thumb and forefinger (or other finger) together to "pinch" the earplug body. Other approaches may also be used to compress the earplug body.

Next, the compressed earplug is inserted into the entrance of an ear canal as part of step 2107 being held in a nominally vertical position as seen in FIGS. 5A, 5B and 5C. Then insertion of the earplug is progressed while allowing it to initially self-align to the extent that may be necessary to have the vertical orientation to better align itself with the ear canal entrance or the earplug may be manually rotated for better alignment. Insertion of the compressed earplug into the ear canal may be accomplished by gripping an external portion of the planar insert between a thumb and forefinger and guiding the earplug into the ear canal with the thumb and forefinger as discussed above. Rocking the earplug up and down in the initial insertion helps with the self-alignment and easy entry. Other fingers may be used to grip and guide the earplug. Alternatively, the earplug may be placed in the entrance to the ear canal, and then pushed into the ear canal by pressing against the back end of the earplug with a finger. Other mechanisms may be used to insert the earplug into the ear canal. In any case the rigidity of the insert allows even rotation of the earplug along its length as may be needed dining insertion for proper orientation with the shape of the ear canal and also to avoid misshaping of the earplug during insertion Finally, after insertion of the earplug into the ear canal for an appropriate and comfortable depth allowing self-adjustment by flexing as may occur, the insertion force for the earplug is removed and the earplug is allowed to be retained in the ear canal. From the point of being compressed at 2105, recovery of the compressed earplug commences and continues until full recovery is done after complete insertion has occurred as at 2110 allowing the earplug to conform to contact with the contours of the ear canal which provides for sound attenuation. As discussed above, the material of the compressible earplug body allows for its compression and slow-recovery expansion of the compressed material a relatively short time after the compressing force is removed.

Figure 21:
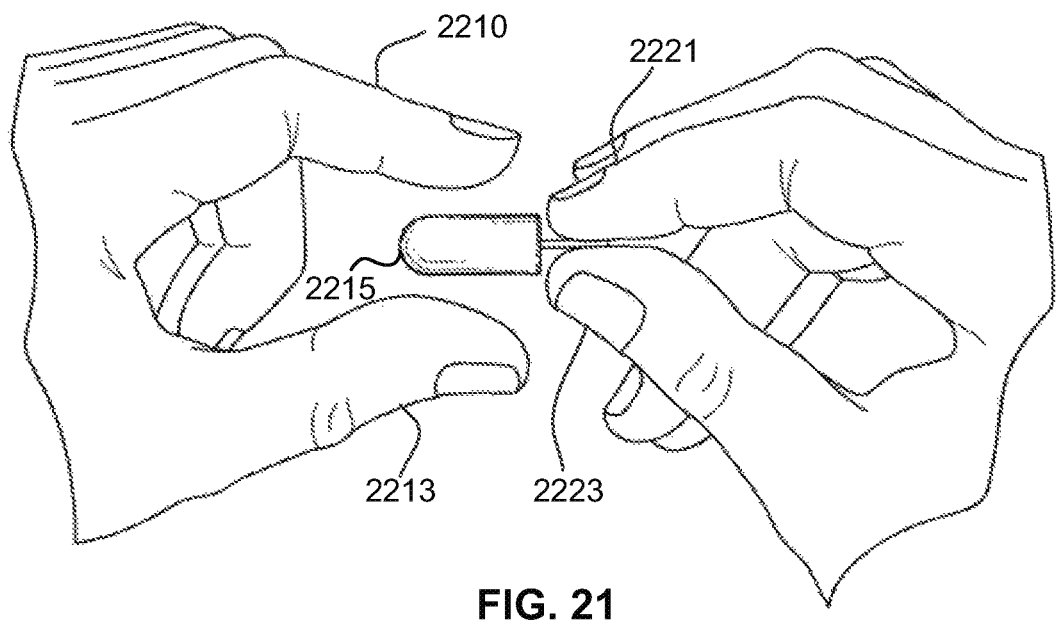
FIG. 21 shows a top view of an earplug held by the thumb and forefinger of one hand ready for being compressed by the thumb and forefinger of another hand.
Figure 22:
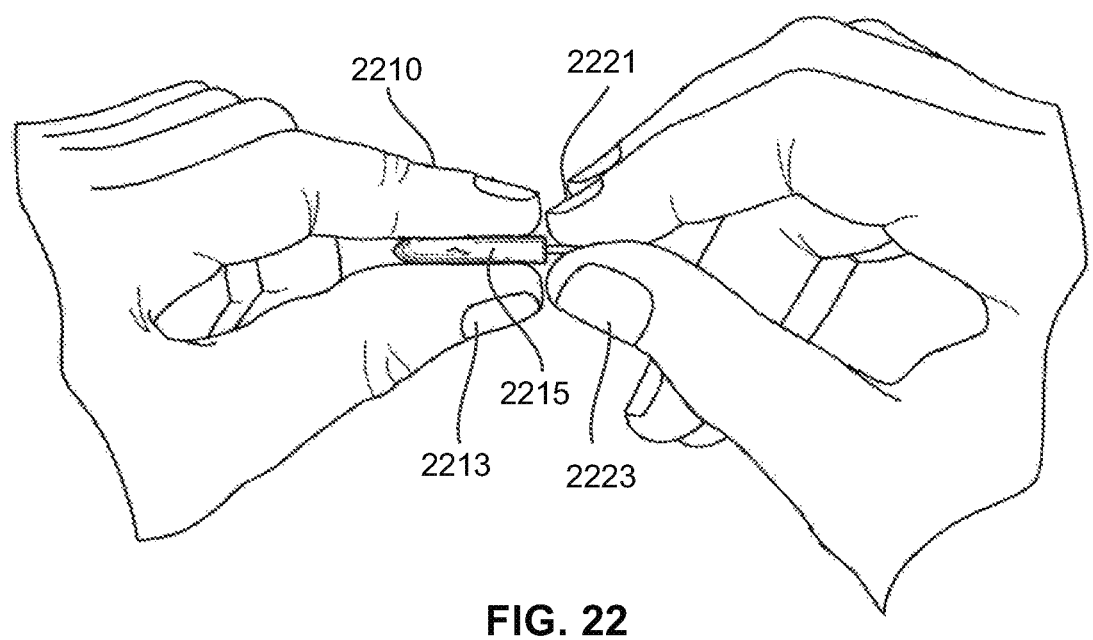
FIG. 22 shows a top view of the earplug being compressed between the forefinger and thumb of one hand while being held by the thumb and forefinger of another hand.
Figure 23:
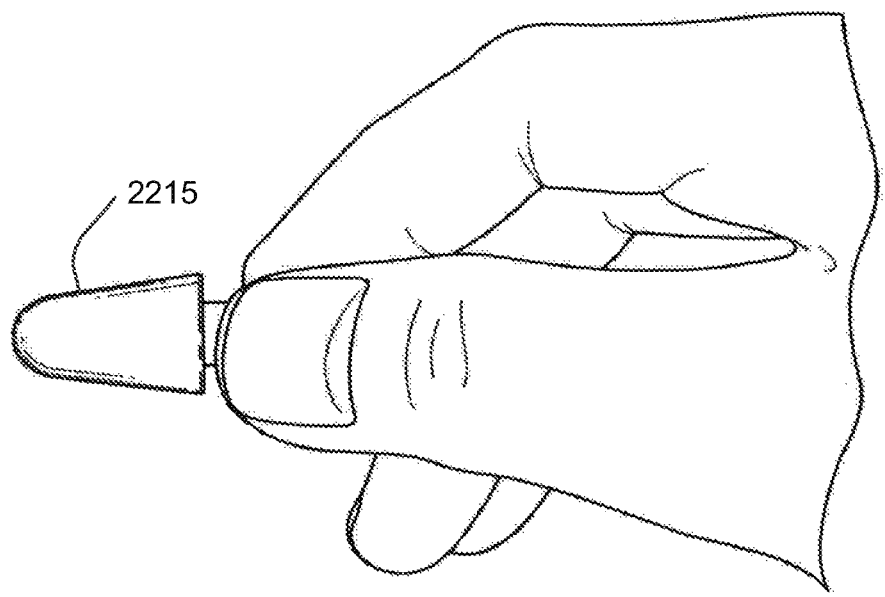
FIG. 23 shows a side view of the earplug after being compressed and being held by the thumb and forefinger of a hand.
Figure 24:
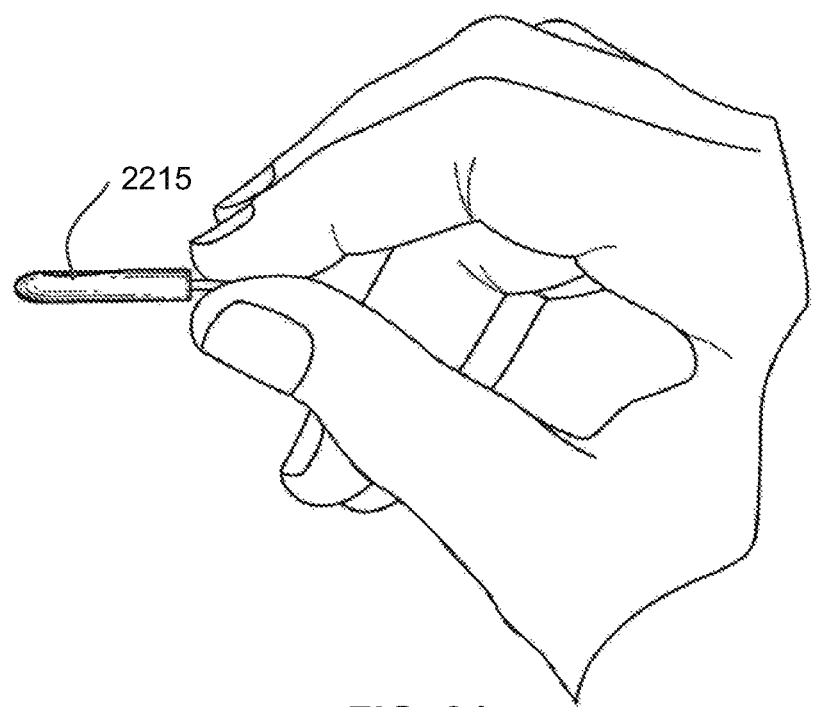
FIG. 24 shows a top view of the earplug after being compressed against the planar surfaces of the planar insert.

FIG. 21 depicts a view of an earplug 2215 held between a forefinger 2221 and a thumb 2223 of a first hand ready to be pinched between a thumb 2213 and a forefinger 2211 of a second hand. FIG. 22 depicts a top view of the earplug 2215 having been pinched to be flattened between the forefinger 2210 and the thumb 2213 of the second hand while held by the thumb 2223 and forefinger 2221 of the first hand. FIG. 23 shows the side view of the earplug 2215 as having been compressed. FIG. 24 shows the top view the earplug 2215 as having been compressed over its entire length, ready to be inserted into the ear canal.

Figure 25A:
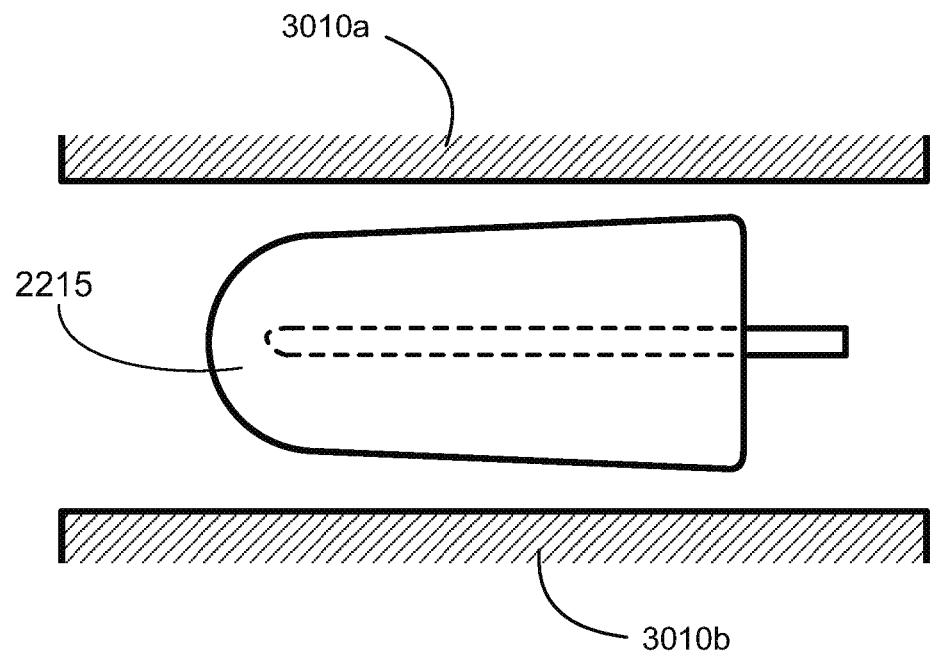
FIG. 25A shows a top view of a compressible earplug positioned ready to be compressed by mechanical surfaces.
Figure 25B:
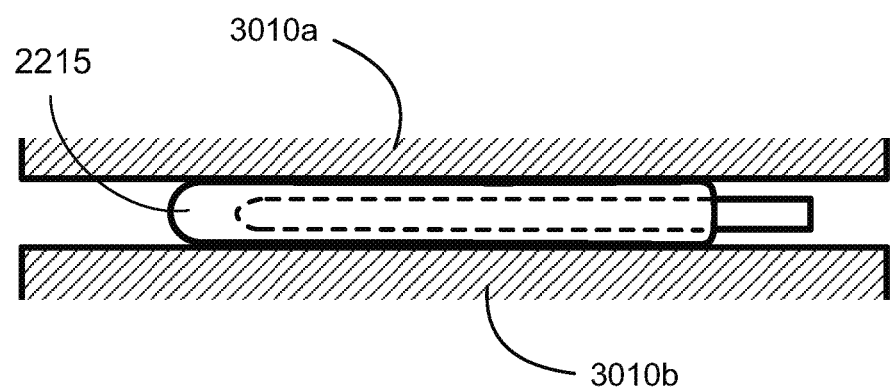
FIG. 25B shows the view of FIG. 25A after compression of the earplug.

FIG. 25A shows how the earplug can be compressed by a mechanism, for example by oppositely spaced surfaces 3010a and 3010b with the earplug 2215 in the space. Then as shown in FIG. 25B, the surfaces 3010a and 3010b are brought together to compress the earplug.

Figure 26A:
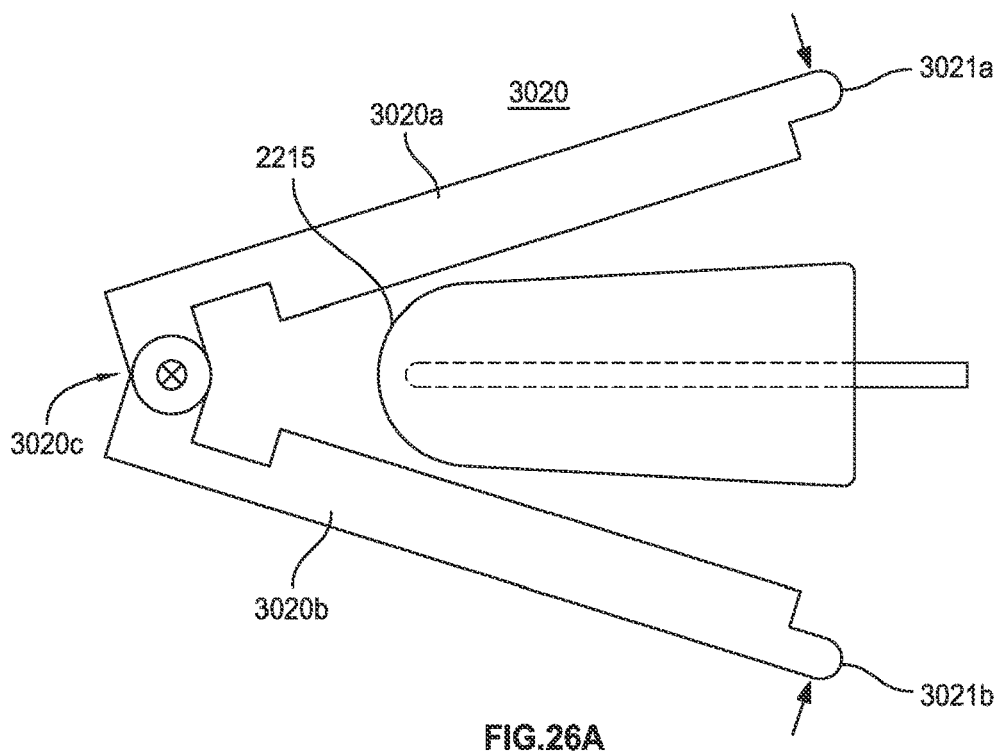
FIG. 26A shows a top view of the tool for compressing an earplug with the earplug in position to be compressed.
Figure 26B:
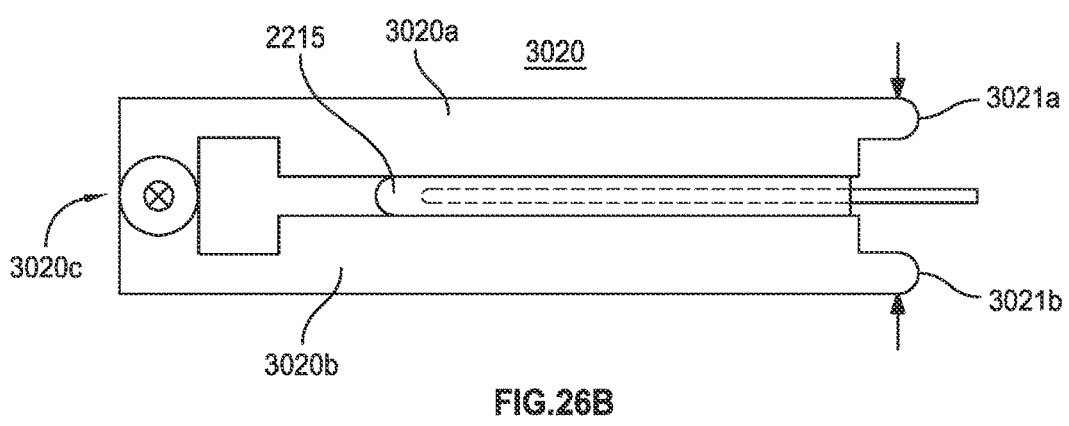
FIG. 26B shows a top view of the tool for compressing the earplug closed and the earplug having been compressed.
Figure 26C:
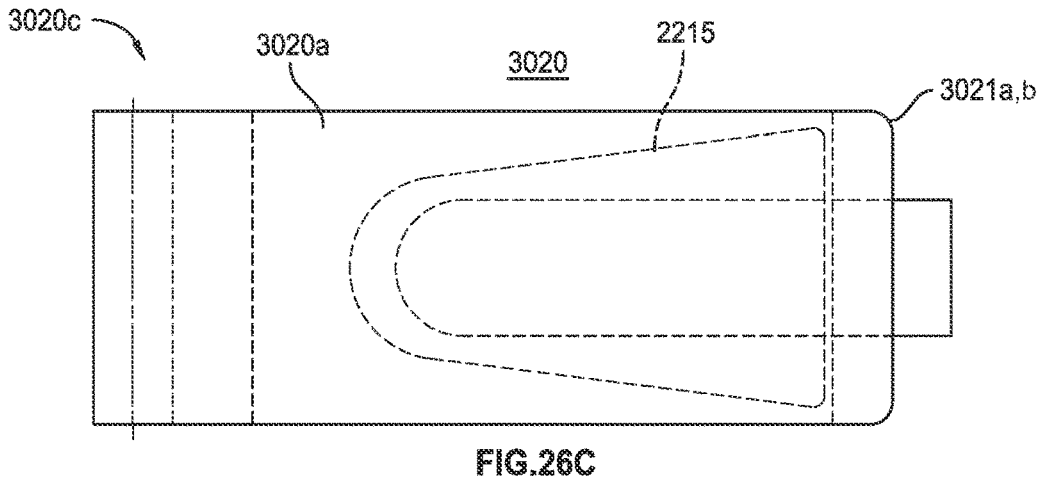
FIG. 26C shows a side view of the compressed earplug in the tool of FIGS. 26A and 26B.

FIGS. 26A, 26B and 26C show a tool 3020 which has an arms 3020a and 3020b rotatably hinged at 3020c. The arms terminated at handles 3021a and 3021b which are for convenient manual operation of the tool. The uncompressed earplug 2215 is placed between the arms 3020a and 3020b which are in opened position in FIG. 26A. Then the arms 3020a and 3020b are rotated (as shown by arrows) to a parallel orientation as in FIG. 26B, wherein the earplug 2215 is compressed to its insertion compressed shape. FIG. 26C shows a top view of the tool 3020 with the earplug 2215 (oriented as a side view of the earplug) inside it.

Although particular embodiments of the invention have been described and illustrated herein, it is recognized that modifications and variations may readily occur to those skilled in the art, and consequently, it is intended that the claims be interpreted to cover such modifications and equivalents.

The invention claimed is:

1. An earplug, comprising:
an earplug body that is elongated and formed from an elastically deformable slow recovery foam, the earplug body being compressible between an uncompressed state and a compressed state; and
a planar insert embedded within the earplug body extending centrally along a center axis of the earplug body, the planar insert comprising a planar internal portion disposed within the earplug body and a planar external portion disposed external to the earplug body, the planar internal portion of the planar insert defining oppositely facing, parallel planar surfaces contacting the earplug body in the uncompressed state and having a length dimension and a height dimension greater than a thickness dimension, the height and thickness dimensions defined as perpendicular to the center axis.

2. The earplug of claim 1, wherein the the external portion is disposed to extend externally from a back end of the earplug body.

3. The earplug of claim 2, wherein the planar insert has one or more holes in it.

4. The earplug of claim 2, wherein the external portion is a continuing extension of the internal portion.

5. The earplug of claim 2, wherein the internal portion has a slot extending lengthwise.

6. The earplug of claim 1, wherein the planar insert comprises a barbed insert.

7. The earplug of claim 6, wherein the barbed insert comprises one or more barbs extending in a plane parallel to the height dimension of the barbed insert.

8. The earplug of claim 1, wherein the planar insert has a tapered shape along its length extending forwardly.

9. The earplug of claim 1, wherein the earplug body has a tapered cylindrical, or bell shape.

10. The earplug of claim 1, wherein the planar insert comprises an internal portion, wherein the internal portion is disposed within the earplug body.

11. The earplug of claim 1, wherein the planar insert comprises material with a higher Young's modulus than material of the earplug body.

12. An earplug for insertion into an ear for providing sound attenuation comprising:
an earplug body comprising compressible slow-recovery foam material having a peripheral surface and a length-extending between a forward termination and a rearward termination;
an entirely planar insert of a flexible resilient material that is more rigid than the earplug body material, the planar insert having an internal portion embedded into the earplug body and an external portion extending outside the rearward termination of the earplug body, the internal portion having a height dimension defined by oppositely facing, parallel planar surfaces, the internal portion extending lengthwise centrally of the earplug body.

* * * * *